United States Patent [19]

Dyckman et al.

[11] Patent Number: 5,504,251
[45] Date of Patent: Apr. 2, 1996

[54] CO-CRACKING OF BPA AND PHENOL PROCESS TARS

[75] Inventors: Arkady S. Dyckman; Andrey V. Zinenkov; Boris I. Gorovits; Valentina Y. Shefter, all of St. Petersburg, Russian Federation; John W. Fulmer, Mt. Vernon; William D. Kight, Poseyville, both of Ind.

[73] Assignee: General Electric Company, Pittsfield, Mass.

[21] Appl. No.: 401,732

[22] Filed: Mar. 9, 1995

[51] Int. Cl.$^6$ ............................................. C07C 37/68
[52] U.S. Cl. ........................... 568/754; 568/724; 568/727; 568/749
[58] Field of Search ..................... 568/724, 749, 568/754, 727, 722

[56] References Cited

U.S. PATENT DOCUMENTS

| | | | |
|---|---|---|---|
| 2,960,494 | 11/1960 | Lewis | 568/754 |
| 3,180,897 | 4/1965 | Sodomann et al. | 568/754 |
| 3,391,198 | 7/1968 | Joris | 568/754 |
| 3,466,337 | 9/1969 | Smith | 568/754 |
| 4,188,496 | 2/1980 | Jaquiss | 568/723 |
| 4,192,954 | 3/1980 | Barker | 568/723 |
| 4,277,628 | 7/1981 | Carnaham | 568/749 |
| 4,485,004 | 11/1984 | Fisher | 208/130 |
| 4,504,364 | 3/1985 | Chen et al. | 568/754 |
| 4,543,177 | 11/1985 | Murthy | 208/130 |
| 5,240,568 | 8/1993 | Chan et al. | 568/754 |
| 5,264,636 | 11/1993 | Shirahata et al. | 568/754 |
| 5,430,200 | 7/1995 | Hood | 568/754 |

Primary Examiner—Werren B. Lone

[57] ABSTRACT

This invention relates to processing of a mixture of tars produced in phenol manufacture and in bisphenol manufacture. The heating of a bottom liquid from a bisphenol-A process together with phenol tar from in a cumene-to-phenol process in a distillation column-type thermal cracking reactor at 290°–360° C. at a mass ratio of 1:(1–10) is employed. The process is carried out by feed entering into the middle of the column and valuable products removed as overhead.

9 Claims, No Drawings

CO-CRACKING OF BPA AND PHENOL PROCESS TARS

This invention relates to bisphenol-A (2,2-bis-p-hydroxyphenylpropane) processing from phenol and acetone, widely used in polycarbonate and epoxide polymer products as well as the processing of phenol and acetone from cumene.

Bisphenol-A is produced by acetone condensation with an excess of phenol in the presence of an acidic catalyst or a cation-exchange resin. The crude product, in addition to bisphenol-A, contains unwanted products, such as p, o'- and o, o'-2,2- hydroxyphenylpropanes, p-isopropenylphenol, and poly-aromatic by-products from secondary condensation and cyclization reactions. During end-product separation by rectification, additional formation of by-products takes place because of further condensation and cyclization reactions in the high temperature zones of the rectification columns. Total amounts of tars thus produced can reach over 10% of commercial product.

Average content of valuable products such as phenol and bisphenols in the tars are 20–60%, but known processing methods to recover such valuable products are subject to technical difficulties and require substantial investment.

Tar by-products are the bottoms of the last rectification column in the usual bisphenol-A plant and ordinarily they are burned or processed by a known method.

There are methods of catalytic decomposition and catalytic hydrodestruction in the presence of hydrogen into lower-boiling products, including initial reagents (phenol and acetone), which can be recycled into the bisphenol-A synthesis process. However, use of complex catalysts, hydrogen, and elevated pressure make such a process expensive and complicated. A series of catalysts is known that provide tar cracking under relatively mild conditions. For example, according to French patent 2364195 (1978) bisphenol tar pyrolysis may be conducted at 150°–250° C. in the presence of sodium hypophosphite, U.S. Pat. No. 4,277,628 (1981) shows the possibility of tar cracking in the presence of aluminum isopropylate providing a good yield of phenol. Usage of alkali catalyst for bisphenol tar decomposition at reduced pressure is described in A.C. CCCP 829610 (1981). U.S. Pat. No. 3,466,337 teaches a tar cracking method with additives of sodium salts of organic and mineral acids. All these methods have disadvantages, such as low yield and high solids formation, which can precipitate in the apparatus, and foul the catalysts. Recycled streams of secondary distillate with traces of catalysts can reduce the activity of the bisphenol-A synthesis catalyst and lead to formation of additional by-products.

Another approach to this problem solution, which eliminates the possibility of passing of catalytic admixtures into the bisphenol-A synthesis zone is isomerisation of tar components into desired products. According to U.S. Pat. Nos. 4,188,496 (1980) and 4,192,954 (1980), bottoms of bisphenol-A remaining from distillation can be diluted with pure phenol in an equivalent mass ratio, the mixture stirred at an average temperature in the presence of dry HBr or HCl gas in an amount of about 4% by weight. The process with HCl takes place at evaluated pressure. Some cases use a triple mixture: tar from distillation, phenol and by-products of tar recovery process. Further treatment includes halogen hydride removal and product crystallization. This method incorporates many stages and special corrosion-resistant equipment, but provide a high bisphenol-A yield.

In this connection, the most available and cheapest procedures employ tar thermal decomposition followed by separation of the lighter components formed in decomposition by rectification, or crystallization, etc.

Phenol tar by-products from the cumene method for phenol and acetone production can be thermocracked by themselves in known processes. This process is carried out at a temperature of 350°–500° C. The thermocracking products are separated by distillation (U.S. Pat. No. 3,391,198 (1968)).

According to A.C. CCCP 1235860 (1986) before decomposition, the phenol tar is diluted by high-molecular weight aromatic compounds such as Baltic shale oil (grade kerogen -70) weight ratio of tar to shale oil 1.3/2.5. Process conditions are: pressure 3–7 MP, temperature 400°–430 ° C., time 5–20 min. Liquid products obtained are separated by distillation. This process takes place under relatively severe conditions and gives a poor yield of phenol (4–5% ) and cumene (10–15% ). In addition it requires the addition of shale oil.

The process closest to the present invention is a method which adds bisphenol-A to the high-boiling bisphenol-A tars in a batch or continuous thermal decomposition operation at 300°–380° C., atmospheric pressure, and continuous removal of the products formed. The ultimate tar residue after cracking in an amount of about 30% of the initial tar is incinerated. The distilled fraction contains 40% phenol, 15% alkylphenols, and a mixture of phenols boiling higher than 270° C. Disadvantages of this process are: low phenol productivity from the bisphenol-A tar components and practically total loss of bisphenol-A, contained in the initial mixture (Z. N. Verhovkaya-Diphenolpropane, Moscow: Chemie, 1971, c.182). An additional problem is the very high viscosity of the bottom liquid and which makes its removal and transfer to incineration very difficult.

So, in spite of the existence of many by-product recovery methods from both BPA and phenol tars, an advantageous method has not yet been found.

In the process of the present invention, thermal decomposition of high-boiling bisphenol-A distillation tar is enhanced in a continuous method employing a thermal cracking reactor at a temperature of from about 290° to about 360° C. with the addition of phenol tar from a phenol-from-cumene process.

This mixture of phenol and bisphenol-A tars can range from substantially all phenol tar with only a very small amount of bisphenol-A tar to substantially all bisphenol-A tar and only a very small amount of phenol tar. Since the bisphenol-A and phenol plants are usually located in close proximity to each other, this thermal cracking reactor is located close by both plants. The levels in the tar feeds are flexible enough to accommodate differing operating rates in the phenol and bisphenol-A plants and still provide the synergism of co-cracking. Thus the weight ratio of bisphenol-A tar to phenol tar may range from about 99:1 to about 1:99, and preferably from about 10:1 to about 1:10. For optimum reduction in viscosity of the heavy bisphenol-A tars a ratio ranging from as low as about one part by weight of bisphenol-A tar to about ten parts by weight of phenol tar to as high as about one part by weight of bisphenol-A tar to about one part by weight of phenol tar is most preferred.

Although any thermal cracking reactor may be used, it is most convenient to use a distillation column type thermal cracker with a pot temperature of from about 290° to about 360° C. A distillation column type reactor conveniently optimizes the separation of the overhead product stream from the bottoms waste stream.

Although control of temperature in the thermal cracker is the key to the present process, it is convenient to conduct the thermal cracking under a pressure ranging from about 0.5 atmospheres to about 20 atmospheres more preferably from about 1 to about 5 atmospheres and most preferably from about 1 to about 3 atmospheres. The average residence time of the tars in the reactor should be sufficient to optimize recovery of phenol, alpha-methylstyrene and cumene but will vary with the configuration of the reaction and the composition of the tars. A typical range for residence time is from about 1 to about 40 hours. In most reactor configurations, the residence times will more preferably range from about 10 to about 30 hours. In a distillation column type reactor the residence time will most preferably be in the range from about 15 to about 25 hours.

The cracking efficiency increases the recovery of valuable products (phenol, α-methylstyrene, cumene). The feed stream enters the middle of the column. The distilled fraction taken off from the top of the column, essentially free from alkyl and alkenyl phenols, is split into two portions, one of which is recycled to the process for recovery of valuable products and the other serves as a reflux to the top of the column. Although a column type reactor with a reboiler pot is the preferred equipment in which to conduct the thermal decomposition any suitable reactor wherein the light ends from thermal decomposition can be removed above the entrance of the feed stream of mixed tars and the heavy ends can be removed below the feed point for disposal. The type of equipment is not critical but the temperature for hydrodecomposition is a key to the efficiency of the process. In a system where residence time in the pot can be closely controlled, the maximum temperature can be as high as about 360° C. although it is preferred to limit the maximum temperature to about 350° C. and for best results to limit the maximum temperature to about 340° C. Similarly, under some circumstances such as where the pot is quite large and residence time is high, the minimum temperature can be as low as about 290° C., but it is preferred to operate no lower than about 300° C. and for best results to limit the minimum temperature to about 310° C. The second key to the process is the ratio of bisphenol-A tar to phenol tar in the mixture fed to the decomposer. The benefit described from mixing the phenol tar and the bisphenol-A tar together is that, in additional to adding materials to the feed composition that act synergistically with the materials in bisphenol-A tar, the phenol tar acts as a solvent for the bisphenol-A tar reducing the viscosity of the tar mixture and allowing the mixture to be more easily handled and transferred. The ratio of the bisphenol-A tar to phenol tar can range from as high as about 1 to about 1 to as low as about 1 to about 10. Where the bisphenol tar tends to be low in viscosity a ratio of more than about 1 to about 1 would be feasible. On the other hand where the bisphenol-A tar is very high in viscosity a ratio less than about 1 to about 10 may be desired. The fully extended limits on the range of ratios for the tar mixture will be readily determined by the skilled artisan. The critical differences of this method compared to those of the prior art are mixing of the tars followed by mutual thermal decomposition (co-cracking) of the high-boiling distillation bottoms from process for making bisphenol-A by condensation of phenol and acetone, the tars from the process for making phenol from cumene at a weight ratio of 1:(1–10) respectively at column pot temperature of 310°–340° C.

Results from this process operation show that these conditions simplify the tar recovery process, make it easier to dispose of the tar bottoms and recover phenol in the fraction containing the desired products which are separated early instead of a mixture of phenol and alkylphenols which is difficult to separate. Moreover, frequently both the bisphenol-A and phenol processes are located near one another, which minimizes transportation cost. All of these benefits increase the efficiency of industrial units for tar processing.

The inventive process is illustrated by the following examples.

In all examples "phenol tar" is a heavy by-product from phenol rectification in the phenol production process by the cumene method. Typically, phenol tar comprises the following main components (% by weight):

| | |
|---|---|
| Phenol | 10–25 wt % |
| Acetophenone | 10–25 |
| Dimethylbenzylalcohol | 3–5 |
| o,p-cumylphenol | 20–40 |
| Alphamethylstyrene dimer | 5–10 |
| Heavy tar | The rest to total 100% |

In the examples "bisphenol-A tar" is a heavy byproduct from bisphenol-A rectification (distillation) in the bisphenol-A production process from phenol and acetone. Typically, the bisphenol-A comprises the following main components (percent by weight);

| | |
|---|---|
| Phenol | 5–20 wt % |
| p,p-bisphenol-A | 15–40 |
| o,p-bisphenol-A | 5–10 |
| IPP dimer | 3–8 |
| Chroman | 5–15 |
| BPX (trimer) | 7–15 |
| Heavy Tar | The rest to total 100% |

IPP means isopropenyl phenol
BPA means bisphenol-A
BPX is a molecule with a molecular weight of 362 and is believed to have the following structure.

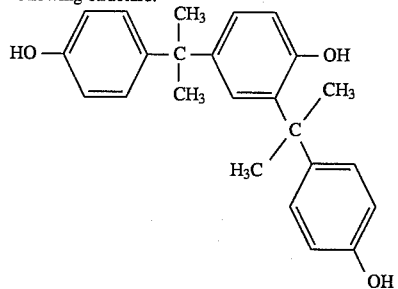

IPP dimer is a molecule with a molecular weight of 268 and is believed to have the following structures.

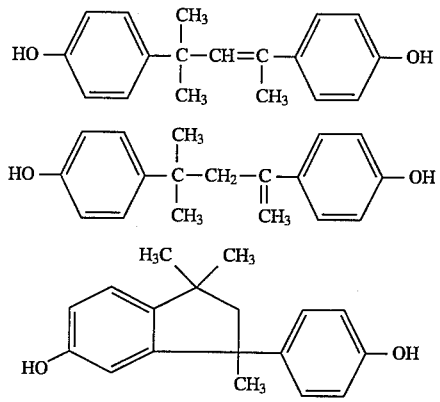

Chroman is a molecule with a molecular weight of 268 and is believed to have the following structure.

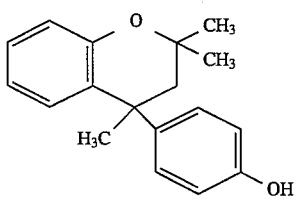

EXAMPLE 1

A mixture of phenol tar and bisphenol tar is decomposed in a unit comprising a continuous rectification column equipped with a total condenser, a 400 ml volume pot and a device providing constant liquid level in the pot. The column is a glass tube having a 15 mm diameter packed with stainless steel spirals. The feed is directed into the middle part of column by a pump from the calibrated heated vessel. The feed rate adjusted to give a residence time of bottom liquid in the pot of 20 hours time. Bottom temperature is 315° C. The column refluxes with overhead product and a reflux ratio of 7–8. The length of the experimental run was 10 hours. The phenol tar/bisphenol tar ratio by weight in the feed was 10/1. Overhead liquid and bottom liquid take off was continuous. Experimental results are presented in Table 1 (Experiment 1).

EXAMPLE 2

The experiment was carried out at the same conditions as in example 1, but the phenol tar/bisphenol tar by weight in the feed was 3/1. Experimental results are presented in Table 1 (Experiment 2).

EXAMPLE 3

The experiment was carried out at the same conditions as in example 1, but the phenol tar/bisphenol tar bay weight in the feed was 1/1. Experimental results are presented in Table 1 (Experiment 3).

EXAMPLE 4

The experiment was carried out at the same conditions as in Example 1, but the bottom temperature was 310° C. Experimental results are presented in Table 1 (Experiment 4).

EXAMPLE 5

The experiment was carried out at the same conditions are in Example 1, but the bottom temperature 340° C. Experimental results are presented in Table 1 (Experiment 5).

EXAMPLE 6

The experiment was carried out at the same conditions as in Example 1, but using only phenol tar as the feed. Experiment results are presented in Table 1 (Experiment 6).

| Experiment # | 1 | 2 | 3 | 4 | 5 | 6 |
| --- | --- | --- | --- | --- | --- | --- |
| Phenol/bisphenol tar ratio | 10 | 3 | 1 | 3 | 3 | — |
| Bottom temperature, °C. | 315 | 315 | 315 | 310 | 340 | 315 |
| Yield, kg/t of feed | | | | | | |
| Phenol | 225.3 | 239.3 | 260.1 | 234.2 | 255.4 | 215.3 |
| α-methylstyrene | 114.3 | 91.5 | 57.8 | 90.4 | 100.2 | 122.0 |
| Cumene | 90.9 | 76.5 | 55.6 | 72.1 | 88.3 | 102.1 |

-continued

| Experiment # | 1 | 2 | 3 | 4 | 5 | 6 |
| --- | --- | --- | --- | --- | --- | --- |
| TOTAL | 430.5 | 407.3 | 373.5 | 396.7 | 443.9 | 439.4 |

The data in Table 1 show, that bisphenol-A tar forms about 300 kg of phenol per 1 ton of bisphenol-A tar (based on the assumption that phenol tar forms an equal amount of products per 1 ton of phenol tar regardless of concentration in all examples).

Decreasing of temperature in the thermodestruction stage lower than 310° C. reduces the yield of valuable products such as (phenol, α-methylstyrene, and cumene. Increasing it higher than 340° C. leads to a considerable rise in viscosity of the bottom liquid making it more difficult to transfer stream to the incinerator. Thus although the thermodecomposition temperature range can be from about 290° C. to about 360° C., it is preferred to operate in the range of from about 300° C. to about 350° C. and most preferred to operate in the range from about 310° C. to about 340° C.

In the present method, the alkenylphenols and alkylphenols, such as IPP, remain in the bottom of the thermocracker as a result of control of reboiler pot temperature and column reflux ratio and exit the reactor in the bottom stream with other waste materials. Since the phenol exits overhead with the other desired products in the product stream, phenol recovery is easily accomplished in a commercial facility by recycling this process stream to the rectification section of a cumene-to-phenol process (see U.S. Pat. Nos. 5,245,090 and 5,245,751 incorporated herein by reference). Alternatively, phenol can be recovered in a separate system using known distillation techniques if, for some reason, it is not desired to recycle the stream to the rectification stage of the phenol process. The high boiling wastes of the bisphenol-A and phenol processes are reduced. Reduction in the level of these wastes is of particular benefit to the environment since their safe disposal is difficult to control and, hence, costly and strictly regulated by government agencies. This salutary benefit is in addition to the productivity gain from the recovery of the phenol, alphamethylstyrene and cumene lost in processes not using this invention. This increases the yields of both the phenol and the bisphenol-A processes. By combining the tars of both processes and thermocracking the mixture, a higher level of the desired products is obtained than by thermocracking either of the waste streams separately. The reduced viscosity of the bottoms of the thermocracker facilitates the transfer of this stream to the incinerator making waste disposal more efficient.

It is convenient to conduct the thermal cracking in a distillation column type reactor. In a distillation column type reactor, the conditions for thermal cracking are readily controlled to remove substantially all of the alkenylphenols and all of the alkylphenols from the reactor as part of the waste stream. No more than about 1% by weight of the overhead stream comprises is alkenylphenols and alkylphenols when maximum throughput through the reactor is required. It is preferred to limit the alkenyl- and alkylphenol content of the overhead to about 0.5 weight percent, more preferred to limit the alkenyl- and alkylphenols to about 0.2 weight percent and most preferred is about 0.1 weight percent.

Thus, the present method allows simplification of the technology for reduction and better utilization of waste products of two different processes: phenol production from cumene and bisphenol-A production from phenol and acetone.

The thermal cracking yields disclosed in the examples are for comparison purposes only and reflect only the recovery of the phenol component. When the value of other recovered tar cracking products such as cumene and alphamethylstyrene is taken into account, the overall productivity enhancement is quite remarkable.

To confirm these laboratory studies, plant trials were conducted in a commercial scale operating plant. The tars in the plant trials were the normal tars out of the phenol from cumene and the bisphenol-A plants.

COMPARATIVE EXAMPLE 7

A plant run of seven days was conducted to establish the maximum level of phenol recovery from phenol tars from the phenol-from-cumene process using the tar cracking process of the prior art.

7 Day Baseline Period: 6652 lb/hr of phenol tar was fed to a thermal cracker and cracked at 321° C. and 20 hrs residence time in the thermal cracker unit. Composition of the phenol tar feed was:

14.0 wt % Phenol
20.0 wt % Acetophenone
22.0 wt % o,p-Cumylphenol
44.0 wt % "high mol wgt tars"

This tar contains "equivalent phenol value" of 1580 lb/hr as calculated below:

| | |
|---|---|
| 6652 × 0.14 = | 931 lb/hr phenol |
| 6652 × 0.22 × 94/212 = | 649 lb/hr phenol from CP |
| | 1580 lb/hr total equiv. phenol |

Average amount of phenol recovered in overheads during the 7 day baseline period: 784 lb/hr.
So:
Cracker Efficiency (Yield)=784/1580=49.6%

EXAMPLE 8

Employing the same conditions as set forth in Example 7, the process of the present invention showed a surprising increase in percent of phenol recovered from the combined tar streams 3 Day Trial Period: 6652 lb/hr of phenol tar and 1531 lb/hr of BPA tar were mixed together and fed to the same thermal cracker unit as in Example 7 and cracked at 321° C. and 20 hr residence time. Tar compositions were as follows:

| | Phenol Tar | BPA Tar |
|---|---|---|
| Phenol | 14.0 | 5.4 |
| Acetophenone | 20.0 | — |
| o,p-Cumylphenol | 22.0 | — |
| p,p-bisphenol A and o,p-bisphenol A | — | 38.0 |
| IPP Dimers | — | 5.1 |
| Chroman | — | 9.6 |
| (BPX) (Trimer) | — | 8.0 |
| Tars | 44.0 | 33.9 |

The above tar mixture contains a total "equivalent phenol content" of 2298 lb/hr as shown calculated below:

| | |
|---|---|
| 6652 × 0.14 = | 931 lb/hr phenol |
| 6652 × 0.22 × 94/212 = | 649 lb/hr phenol from CP |

| | |
|---|---|
| | 1580 lb/hr phenol from Phenol Tar |
| 1531 × 0.054 = | 83 lb/hr phenol |
| 1531 × 0.38 × 188/228 = | 480 lb/hr phenol from BPA |
| 1531 × 0.051 × 188/268 = | 55 lb/hr phenol from IPP Dimer |
| 1531 × 0.08 × 282/402 = | 86 lb/hr phenol from BPX |
| 1531 × 0.096 × 94/268 = | 52 lb/hr phenol from Chroman |
| | 756 lb/hr phenol from BPA Tar |

Average amount of phenol recovered in overheads during the 3 day trial period: 1525 lb/hr.

Overall Cracker Efficiency=1625/2336=69.6%
This shows that an unexpected "synergism" occurs when BPA tar is admixed with phenol tar, i.e: 1625−756=869 lb/hr phenol is recovered from phenol tar itself.
So:
869/1580=55% cracking efficiency achieved when BPA tar is present to act as "catalyst" for the phenol tar.

This compares with baseline of only 784 lb/hr when phenol tar was cracked alone, i.e. only 49.6% cracking efficiency. In addition to this increase in efficiency of phenol tar cracking, the recovery of phenol value from BPA tar was nearly quantitative.

The mixing and co-cracking of the two "tar" streams gave an unexpected mutual synergistic effect, resulting in phenol recoveries higher than predicted by standard chemistry. Current wisdom teaches that when BPA is thermally decomposed, the result is one mole of phenol and one mole of IPP. The IPP is not expected to further de-alkylate to phenol and propane.

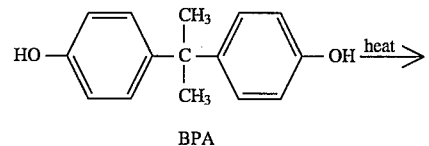

BPA

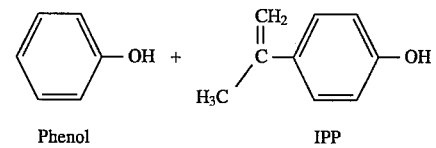

Phenol                IPP

However in this invention, the BPA, IPP dimers and other isomeric by-products contained in the BPA tar, do seem to dealkylate in part to yield additional phenol. This is believed to be the reason for the unexpected high yields which are achieved during co-cracking:

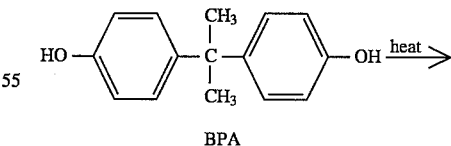

BPA

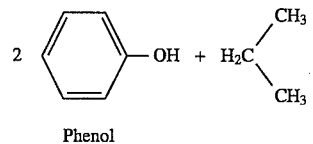

Phenol

In addition, the BPA tar contains "acidic" components which act to lower the pH of the mixed feed stream and cause the co-cracking operation to be performed under an "acid cracking regime", whereby higher yields of phenol are obtained from the phenol tar.

The foregoing examples and experimental and predictive results are meant to explain and describe the invention, and are not intended to limit the invention to only those parameters specifically disclosed. Thus, upon perusing this specification, various modifications of the foregoing description may become apparent, and such are intended to be within the scope and spirit of the invention as defined by the following claims.

The invention claimed is:

1. A method for recovering phenol, alpha-methylstyrene and cumene from a mixture of a bisphenol-A tar from a process for production of bisphenol-A by the condensation of phenol and acetone and a phenol tar from a process for the production of phenol from cumene comprising mixing bisphenol-A tar with phenol tar and thermally decomposing the tars at a temperature ranging from about 290° C. to about 360° C.

2. The method of claim 1 wherein the temperature ranges from about 300° C. to about 350° C.

3. The method of claim 2 wherein the temperature ranges from about 310° C. to about 340° C.

4. The method of claim 1 wherein the thermal decomposition is conducted in distillation column-type reactor.

5. The method of claim 4 which additionally comprises withdrawing from the reactor a product stream comprising phenol, alphamethylstyrene and cumene and recycling the product stream to a cumene hydroperoxide decomposition products rectification system of the phenol-from-cumene process.

6. The method of claim 5 which additionally comprises withdrawing from the reactor a waste stream comprising an alkylphenol and an alkenyl phenol.

7. The method of claim 6 wherein the product stream is removed as an overhead stream from the reactor and the waste stream is removed as a bottoms stream from the reactor.

8. The method of claim 7, wherein the alkylphenol and alkenylphenol are substantially all removed from the reactor in the bottoms stream and no more than about one percent by weight of the alkylphenol and the alkenylphenol are in the overhead stream.

9. The method of claim 1 wherein no catalyst is added to the mixture whereby recovered product purification is simplified since no catalyst residues are present.

* * * * *